United States Patent
Deneer

(10) Patent No.: US 10,499,577 B2
(45) Date of Patent: Dec. 10, 2019

(54) WHITE CELERY

(71) Applicant: RIJK ZWAAN ZAADTEELT EN ZAADHANDEL B.V., De Lier (NL)

(72) Inventor: Reinier Hendrik Marie Deneer, De Lier (NL)

(73) Assignee: RIJK ZWAAN ZAADTEELT EN ZAADHANDEL B.V., De Lier (NL)

( * ) Notice: Subject to any disclaimer, the term of this patent is extended or adjusted under 35 U.S.C. 154(b) by 0 days.

(21) Appl. No.: 15/837,148

(22) Filed: Dec. 11, 2017

(65) Prior Publication Data
US 2018/0116145 A1  May 3, 2018

Related U.S. Application Data

(63) Continuation-in-part of application No. PCT/EP2016/065644, filed on Jul. 4, 2016.

(30) Foreign Application Priority Data
Jul. 3, 2015 (EP) ................. 15175333

(51) Int. Cl.
A01H 5/04 (2018.01)
C12Q 1/6895 (2018.01)
A01H 1/04 (2006.01)
A01H 5/12 (2018.01)
A23L 19/00 (2016.01)
A23L 33/105 (2016.01)

(52) U.S. Cl.
CPC ............ *A01H 5/04* (2013.01); *A01H 1/04* (2013.01); *A01H 5/12* (2013.01); *A23L 19/09* (2016.08); *A23L 33/105* (2016.08); *C12Q 1/6895* (2013.01); *A23V 2002/00* (2013.01); *C12Q 2600/13* (2013.01); *C12Q 2600/158* (2013.01)

(58) Field of Classification Search
None
See application file for complete search history.

(56) References Cited

U.S. PATENT DOCUMENTS

2014/0030389 A1* 1/2014 Pierce ............ A23L 19/05
426/100

FOREIGN PATENT DOCUMENTS

WO 2009/114954 9/2009

OTHER PUBLICATIONS

International Search Report and Written Opinion of the International Searching Authority dated Sep. 16, 2016, which issued during prosecution of International Application No. PCT/EP2016/065644.
Fu, et al. "De Novo Assembly, Gene Annotation and Marked Development Using Illumina Paired-End Transcriptome Sequences in Celery (*Apium graveolens* L.)" Feb. 2013, PLos One 8(2):e57686.
Han, et al. "Inheritance of white petiole in celery and development of a tightly linked SCAR marker" Plant Breeding, Apr. 2012, 131(2):340-344.
Sellami, et al. "Essential oil and aroma composition of leaves, stalks and roots of celery (*Apium graveolens* var. dulce) from Tunisia" The Journal of Essential Oil Research, Dec. 2012, 24(6):513-521.
United States Department of Agriculture "Plants Profile for *Apium graveolens* dulce (wild cherry)" Jan. 2015, retrieved from http://plants.usda.gov/core/profile?symbol=APGRD.
Wang, et al. "Genetic diversity in *Apium graveolens* and related species revealed by SRAP and SSR markers" Scientia Horticulturae, Mar. 2011, 129(1):1-8.

* cited by examiner

*Primary Examiner* — Bratislav Stankovic
(74) *Attorney, Agent, or Firm* — Duane Morris LLP; Thomas J. Kowalski; Deborah L Lu

(57) ABSTRACT

The invention relates to a celery plant (*Apium graveolens* L. *dulce*) carrying a genetic determinant that leads to the absence or strong reduction of chlorophyll in the petioles, wherein said determinant is obtainable by introgression from a plant grown from seed of which a representative sample was deposited with the NCIMB under deposit number NCIMB 42428. The invention further relates to markers and the use of markers for the identification of a plant that has an absence or strong reduction of chlorophyll in the petioles. The invention also relates to seeds and other propagation material of the plant and to its progeny as well as to food products that comprise the consumable parts of the plant.

14 Claims, 3 Drawing Sheets
(1 of 3 Drawing Sheet(s) Filed in Color)

Specification includes a Sequence Listing.

Fig. 3

SNP marker sequences white celery

SEQ ID No. 1 - SNP on position 175
TTWARGCAGTGTGGATACCTCAGATTGAATAGCCACACTTTTGCTCACAAGGTCAGTGGTGGTTATTGCAA
CAGCTGCCGAATCTGCCCTATTGAAAACAAAGATCTACGTTTCAGATAGGATATGAAGAATAATAAAATGA
TCATGCTATCTACATCTGTAATTAGAAAAACATAGAGAGCAAAAATGACTGCCAAAAAATTTCAACGGAAA
ACAGATCCAACATATATAGTAAGTGCTCTGTAAATCAGTTTTCCGCATGATATCAGGTGAAAAAGTGTACC
CTGCAG SEQ ID No. 2 - SNP on position 261
TTAACCATCATTGATTATGATCTTGTTTTATCGAATTATATTGTTTATCATATTRAACTGCTTTAGGATTGGA
TAGTTTTTATATATGTGGACCAGATTCGTGGTCAGACCATACCAATGGTCAAGTTAGGCCAATGTGTGCCTT
GGATCCAGTAATTAGAGCAGTGTTKTGTGCTTGCTCGGGGTTAGTGCGTGACTGAKCAGCAGCCTAACCTT
GGTTTTTAAAACTTAAATATGCTGTGAAAGAATAAGATCCACACTCCTATTACTATAATTTCTTTGAAGATT
GTCAAATAACTCATTCTTTGAAGCATGTGCAGAAATTTTAGTCTGACAAAATACAGAAGGGAATTGGAAAA
TTGGTTTAGTGTAACTAGACTAGTCYTGATAATGCATCGAAGTTCAGTGATAGAATGCAAAGAACCATATA
TCCAAAAATTCTATATCAAAGCTAGATCAGTACCTGCAG SEQ ID No. 3 - SNP on position 175
TTAAAATAATTGTGGAGGTAAACTGARKTTTTTTTKKCTAAGTAAACTCACACACACACAGGGGTTGAACC
CTTGACCTCCTCCAGAGGAGGCAAGAGCTCAAGCACTGCACCAACCCTTTGTTGGCAAGGTAAGCAGAGTT
ATTCACAAACAAATGTCTACTTTTTTCTGATCGAGCAGAAGTTAGCTCATTTGCAGATGAATGTGTGAGAAT
GTCCAATAATTTAGGCACCTTTGAAGAAATCACCTATTTCCCTGCAG SEQ ID No. 4 – 1 nucleotide insertion on position 57
CTGCAGGTACTACAATTAGAATCTAAATTGCTCAGGTACAGAAAAGGTTTAGTGAACGATTTCTAAAACCA
GGATGGTGAAATTGGACCACAAGATTTTGTATCATCTCTGGTTTCATACTAAAAGTAGATTTATACTAACAC
TTATTTGGCCCATTTAATAATCATAAACATGAGAAAAAAGATAAACCATAATAATTTACTTGTATAGAATTA
GAAGAAACCAGAACATGATAGGATATAATAAGTCAGTG

WHITE CELERY

RELATED APPLICATIONS AND INCORPORATION BY REFERENCE

This application is a continuation-in-part application of international patent application Serial No. PCT/EP2016/065644 filed Jul. 4, 2016, which published as PCT Publication No. WO 2017/005669 on Jan. 12, 2017, which claims benefit of European patent application Serial No. 15175333.2 filed Jul. 3, 2015.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

SEQUENCE LISTING

The instant application contains a Sequence Listing which has been submitted electronically in ASCII format and is hereby incorporated by reference in its entirety. Said ASCII copy, created on Dec. 7, 2017, is named 43104_00_2342_SL.txt and is 3,322 bytes in size.

FIELD OF THE INVENTION

The present invention relates to a new type of celery (*Apium graveolens* L. *dulce*) with a genetically based altered appearance. The invention further relates to markers linked to the genetic determinant and the use of markers to identify the genetic determinant. The invention also relates to the seeds and progeny of such plants and to propagation material for obtaining such plants.

BACKGROUND OF THE INVENTION

*Apium graveolens* is a plant species in the family Apiaceae. The species consists of several morphologically distinct botanical varieties, each of which is used for a different purpose. The most important types are celery or stalk celery, which is designated *Apium graveolens* L. *dulce*; celeriac or root celery, which is designated *Apium graveolens* var. *rapaceum*; and smallage or leaf celery, which is designated *Apium graveolens* var. *secalinum*.

In celery or stalk celery (*Apium graveolens* L. *dulce*), the part that is consumed is the petiole of the leaf, which is greatly enlarged. The petiole or 'stalk' quality, which covers many aspects, is one of the most important characteristics in breeding new celery varieties. This is therefore also the main characteristic that distinguishes var. *dulce* from var. *rapaceum* and var. *secalinum*, which do not have the solid, firm, thick, and long petioles that characterize var. *dulce*.

In certain areas a stalk celery type called 'white celery' is marketed. A lower amount of chlorophyll in the stalks renders characteristics to the crop which are greatly favored by a number of consumers. To produce 'white celery', common stalk celery is grown on ridges in the field. While the celery is growing, the stalks are blanched by covering them up with soil, called 'earthing up', to prevent chlorophyll from developing in the stalks through the direct influence of sunlight. The resulting celery plants have a much lighter green or whitish color, which is subsequently marketed as a premium crop, 'white celery'.

Because of the intensive process that is necessary for obtaining 'white celery', as well as the additional cleaning that is required after harvest, the production of 'white celery' is very costly and labor intensive.

In other regions, such as in Italy, a type called 'sedano bianco' (white celery) is produced, of which the best known variety is called 'Sedano Bianco di Sperlonga', without covering up the stalks to protect them from direct sunlight. These stalks however are indeed naturally lighter green than common stalk celery, but certainly not white. The same holds for so-called 'self-blanching' celery, which also has a lighter green color than regular green stalk celery.

Citation or identification of any document in this application is not an admission that such document is available as prior art to the present invention.

SUMMARY OF THE INVENTION

It is an object of the present invention to provide a new type of truly white celery that does not require protection from direct sunlight to obtain its white color.

The invention thus relates to a celery plant of the species *Apium graveolens* L. *dulce* carrying a genetic determinant that leads to genetically white stalk celery. The new celery plant of the invention can be grown in the presence of direct sunlight, since the genetic determinant leads to an absence or strong reduction of chlorophyll in the petioles independently of the presence of light.

In one embodiment, the invention thus relates to a celery plant (*Apium graveolens* L. *dulce*) carrying a genetic determinant that leads to an absence or strong reduction of chlorophyll in the petioles, which genetic determinant may be as comprised in an *Apium graveolens* L. *dulce* plant, representative seed of which was deposited with the NCIMB under deposit number NCIMB 42428. Such a celery plant of the invention therefore has the same genetic determinant as the genetic determinant that is present in deposit NCIMB 42428.

In one embodiment, said determinant is introgressed from, or is obtainable by introgression from, a plant, preferably an *Apium graveolens* L. *dulce* plant, which may comprise said genetic determinant, representative seed of which was deposited with the NCIMB under deposit number NCIMB 42428.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC.

All rights to explicitly disclaim any embodiments that are the subject of any granted patent(s) of applicant in the lineage of this application or in any other lineage or in any prior filed application of any third party is explicitly reserved Nothing herein is to be construed as a promise.

It is noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

DEPOSIT

Seeds of *Apium graveolens* L. *dulce* S14.28078 that comprise the genetic determinant and phenotypic trait of the invention were deposited with NCIMB Ltd, Ferguson Building, Craibstone Estate, Bucksburn, Aberdeen AB21 9YA, UK on Feb. 7, 2015 under deposit accession number NCIMB 42428.

The Deposit with NCIMB Ltd, under deposit accession number NCIMB 42428 was made pursuant to the terms of the Budapest Treaty. Upon issuance of a patent, all restrictions upon the deposit will be removed, and the deposit is intended to meet the requirements of 37 CFR §§ 1.801-1.809. The deposit will be irrevocably and without restriction or condition released to the public upon the issuance of a patent and for the enforceable life of the patent. The deposit will be maintained in the depository for a period of 30 years, or 5 years after the last request, or for the effective life of the patent, whichever is longer, and will be replaced if necessary during that period.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following detailed description, given by way of example, but not intended to limit the invention solely to the specific embodiments described, may best be understood in conjunction with the accompanying drawings.

FIG. 3 gives the sequences of SEQ ID NOS. 1-4.

DETAILED DESCRIPTION OF THE INVENTION

Figure 1:
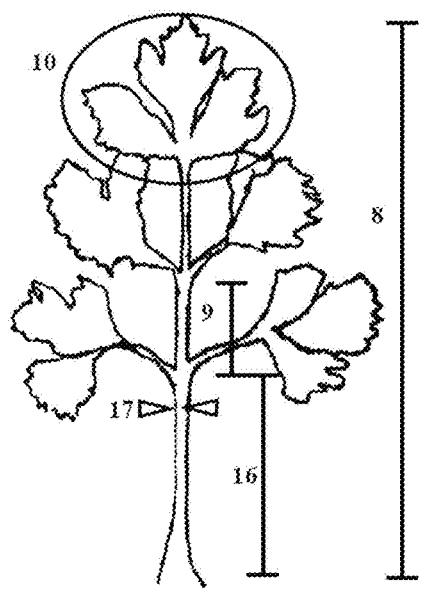
FIG. 1 illustrates the description of a celery leaf according to UPOV TG/82/4. Reference numeral 8 refers to the leaf length including the petiole. Numeral 9 represents the distance between $1^{st}$ and $2^{nd}$ pair of leaflets. 10 is the size of the terminal leaflet. Numerals 16 and 17 refer to the length (16) and width (17) of the petiole.

"Introgression" as used herein is intended to mean introduction of a trait, by introgressing the genetic determinant leading to that trait, into a plant not carrying the trait by means of crossing and selection in a generation in which the trait becomes visible, or in which the genetic determinant can be selected either phenotypically or with the use of markers.

The trait of the present invention, which trait is the absence or strong reduction of chlorophyll in the petioles of *Apium graveolens* L. *dulce*, leading to white petioles, is a dominant trait. A dominant trait is visible in the F1 of a cross between a parent plant with the trait and a parent plant without the trait. When the parent plant with the trait of the invention is homozygous for the genetic determinant, all F1 plants will have the trait. After crossing the F1 with itself or with another plant, the subsequent generation can segregate for plants with and without the trait, and selection can take place. The genetic determinant of the present invention can be present in homozygous or heterozygous state to result in the phenotypic trait of the invention. The trait of the invention inherits as a monogenic trait.

It should be noted that if the selection criterion or criteria is or are clearly defined, the skilled person will be able to identify the descendants that carry the trait in any further generation. With respect to the determinant of the invention that underlies the absence or strong reduction of chlorophyll in the petioles, plants that carry the determinant can suitably be identified among descendants from a cross between a plant not carrying the determinant and a plant that does carry the said determinant and of which representative seed was deposited under deposit number NCIMB 42428, by growing F2 plants from seeds that are the result from the initial cross and a selfing step, and selecting plants showing the desired trait phenotypically or with the use of markers.

In one embodiment the presence of the genetic determinant that leads to an absence or strong reduction of chlorophyll in the petioles of a celery plant can be identified by any of the markers having SEQ ID NO. 1, SEQ ID NO. 2, SEQ ID NO. 3, and/or SEQ ID NO.4, or a combination of these SEQ ID NOS. (FIG. 3). In a preferred embodiment the genetic determinant can be identified by the use of SEQ ID NO. 1 as a marker.

In one embodiment the genetic determinant may be as comprised in NCIMB 42428 is linked to any of the markers having SEQ ID NO. 1, SEQ ID NO. 2, SEQ ID NO. 3, and/or SEQ ID No.4, in particular to the marker having SEQ ID NO. 1. In deposit NCIMB 42428 the genetic determinant is linked to at least one of the markers having SEQ ID NO. 1, SEQ ID NO. 2, SEQ ID No. 3, and/or SEQ ID NO.4, in particular to the marker having SEQ ID NO. 1.

Mapping of the genetic determinant of the invention resulted in the identification of four markers that are closely linked to the trait, and can be used for identification of the trait. The markers indicated with SEQ ID NOS. 1-3 are SNP markers, which each have a SNP at the below position of the sequences as represented in FIG. 3. For SEQ ID NO. 1 this is a change from C to T at position 175; for SEQ ID NO. 2 the SNP is a change from C to T at position 261; and for SEQ ID NO. 3 the SNP is a change from A to G at position 175. The marker indicated with SEQ ID No. 4 has an insertion of 1 bp which insertion is a C, at position 57 of the sequence of FIG. 3.

The leaves of *Apium graveolens* L. *dulce* are compound leaves that are composed of a petiole, or leaf stem, and a fully subdivided leaf blade. The leaf blade starts at the first joint on the petiole. The leaf blade consists of several pairs of leaflets, attached to the central leaf stem by 'secondary petioles' which are called petiolules, and ends with a terminal leaflet. A petiole and its leaf blade together form a leaf of the celery plant (FIG. 1).

A plant of the present invention may comprise at least white petioles, which are petioles that are absent or strongly reduced in chlorophyll content. The petioles are also called 'stalks'. Optionally, the petiolules of the leaflets are also absent or strongly reduced in chlorophyll content.

The absence or strong reduction of chlorophyll in the petioles of *Apium graveolens* L. *dulce* is preferably observed when the plants are past the seedling stage up till the moment that they are mature. Plants are considered to be past the seedling stage after a growing period of at least 6 weeks, and they are usually transplanted at about 6-8 weeks after sowing. Celery plants are considered to be mature and ready for harvest at about 100-120 days after transplanting. The absence or strong reduction of chlorophyll in the petioles is easily observed by the white color of the petioles in this period between transplanting and harvest.

Optionally, chlorophyll can be measured in a sample of the petiole tissue of an *Apium graveolens* L. *dulce* plant. Again, a chlorophyll measurement is preferably performed between 6 weeks after sowing and 120 days after transplanting, i.e. past the seedling stage up till the mature stage of the plants. In early stage, at 2 after transplanting, the petioles of a plant of the invention have an average total chlorophyll content that in order of increased preference is lower than 100 µg/g, 80 µg/g, 60 µg/g, 40 µg/g. In order to determine whether a plant has the average total chlorophyll content of the invention, at least 5 plants of the same line are measured with the method as described in Example 2. A normal amount of chlorophyll, as used herein, or a total chlorophyll content that is not reduced, is a chlorophyll content which is higher than 120 µg/g. Total chlorophyll content as used herein is the content of chlorophyll a+chlorophyll b.

In mature stage, at 14 weeks after transplanting, the total chlorophyll content in the petioles of a plant of the invention is lower than 4 µg/g, which is below the determination limit of the method as used in Example 2. At this plant stage, a normal amount of chlorophyll, or a chlorophyll content that is not reduced, is a chlorophyll content which is higher than 4 µg/g, or which is higher than 5 µg/g when an average of at least 5 plants is taken.

The presence of pigments in plant parts is essential for the development of a plant. The presence of chlorophyll in particular is necessary for the green plants parts to be able to carry out photosynthesis, and subsequently to attain growth and development. Plants that have a lack of chlorophyll, and therefore show chlorophyll deficiency, have major problems in obtaining normal plant growth.

In addition, various types of carotenoids and anthocyanins are vital in protecting plants against light irradiation or an excess of light, which can result in serious photo-inhibition or photo-damage. Carotenoids are generally yellow to orange, and anthocyanins red to purple, but although they are not directly visible, they are also commonly present in the green photosynthetic plant parts where they play an important protective role.

Plants that have a total lack of pigments such as chlorophyll, carotenoids, and anthocyanins, will be all white. Totally white plants are commonly referred to as 'albino' plants. Without supplementing essential nutrients and/or hormones, as well as growing them in a controlled and protected environment, albino plants will not be able to develop properly and will die after a very short time.

Plants that are not completely but only partly white will usually be able to grow, but will generally be weaker than their standard green version. Reduction of the total amount of chlorophyll in a plant will lead to reduction of photosynthesis, and thereby to weaker growth and less vigorous plants. The more substantial share the plant parts lacking in chlorophyll form of the total plant, the more reduction in growth is expected.

Moreover, since white plant parts lack the pigments that protect them from photo-inhibition or ultimately photo-damage resulting from excess light, partially white plants are often very difficult to grow under normal light conditions.

A celery plant of the invention having white petioles surprisingly shows a similar growth and/or vigor as a celery plant that has a normal amount, i.e. no reduction, of chlorophyll in the petioles. A similar growth and/or vigor means that, after a standard growing period of 3-4 months from transplanting, the celery plant has reached an average size as is common for a commercially available reference celery plant. An example of such reference plant is the commercially available variety Kelvin F1.

According to a further aspect of the invention the white petioles of an *Apium graveolens* L. *dulce* celery plant of the invention are solid.

The *Apium graveolens* L. *dulce* plant of the invention is obtainable by crossing a first celery plant with a second celery plant, wherein at least one of the said plants is grown from seed that carries the genetic determinant as found in the genome of a plant, representative seed of which was deposited with the NCIMB under deposit number NCIMB 42428, or a progeny plant thereof, optionally crossing the resulting F1, and selecting for plants that have an absence or strong reduction of chlorophyll in the petioles and/or a white color of the petioles. Subsequently, one or more additional rounds of crossing and/or selection can be done.

Suitably, before selecting, one or more further crossing steps can first be performed until a generation is obtained in which selection is deemed to be useful. Selection is in principle performed in a population in which the trait of the invention segregates. Markers can be used to select for plants having the genetic determinant either homozygously or heterozygously. Crossing may comprise selfing, i.e. crossing with itself, and crossing with any other *Apium graveolens* plant that does or does not have the trait of the invention.

The parent that provides the genetic determinant that leads to the trait of the invention is not necessarily a plant grown directly from the deposited seeds. The parent can also be a progeny plant from the deposited seed, obtained by for example selfing or crossing, or any other plant obtained by other means that is identified to comprise the genetic determinant that leads to the trait of the invention.

The invention furthermore relates to a cell of a *Apium graveolens* L. *dulce* plant as claimed. Such cell may be either in isolated form or may be part of the complete celery plant or parts thereof and then still constitutes a cell of the invention because such a cell harbors in its genetic constitution the genetic information that leads to the characteristics that define the new celery type. Each cell of a celery plant of the invention carries the genetic information that leads to phenotypic expression of said trait. Such a cell of the invention may also be a regenerable cell that can be used to regenerate a new celery plant of the invention. In the context of this application "of the invention" means carrying a genetic determinant as found in NCIMB 42428, which leads to an absence or strong reduction of chlorophyll in the petioles at least at six weeks after sowing, which is expressed as white petioles.

The invention also relates to tissue of a plant as claimed. The tissue can be undifferentiated tissue or already differentiated tissue. Undifferentiated tissues are for example stem tips, anthers, petals, pollen and can be used in micropropagation to obtain new plantlets that are grown into new plants of the invention. The tissue can also be grown from a cell of the invention.

The invention according to a further aspect thereof relates to *Apium graveolens* L. *dulce* seed, wherein the plant that can be grown from the seed is a plant of the invention, which may comprise the genetic determinant that leads to an absence or strong reduction of chlorophyll in the petioles. The invention also relates to seeds of a plant as claimed. Although the seeds do not show the characteristics of the celery of the invention they harbor the genetic information that when a plant is grown from the seeds makes this plant a plant of the invention.

The invention also relates to progeny of the plants, cells, tissues and seeds of the invention, which progeny may comprise the genetic determinant that leads to an absence or strong reduction of chlorophyll in the petioles. Such progeny can in itself be plants, cells, tissues or seeds.

As used herein the word 'progeny' is intended to mean the first and all further descendants from a cross with a plant of the invention that has white petioles, which white petioles are caused by the presence of a genetic determinant that leads to a reduction or strong absence of chlorophyll, wherein said genetic determinant is as found in seeds deposited under NCIMB deposit No. 42428.

'Progeny' also encompasses plants that carry the genetic determinant of the invention and have the trait of the invention, and are obtained from other plants or progeny of plants of the invention by vegetative propagation or multiplication. Progeny of the invention suitably may comprise the genetic determinant and the trait of the invention.

The invention thus further relates to parts of the plant that are suitable for sexual reproduction. Such parts are for example selected from the group consisting of microspores, pollen, ovaries, ovules, embryo sacs and egg cells. In addition, the invention relates to parts of the plant that are suitable for vegetative reproduction, which are in particular cuttings, roots, stems, cells, protoplasts. The parts of the plants as mentioned above are considered propagation material. The plant that is produced from the propagation material may comprise the genetic determinant that leads to an absence or strong reduction of chlorophyll in the petioles.

According to a further aspect thereof the invention provides a tissue culture of a plant carrying the genetic determinant of the invention, which is also propagation material. The tissue culture may comprise regenerable cells. Such tissue culture can be selected or derived from any part of the plant, in particular from leaves, pollen, embryos, cotyledon, hypocotyls, meristematic cells, roots, root tips, anthers, flowers, seeds and stems. The tissue culture can be regenerated into a plant carrying the genetic determinant of the invention, which regenerated plant expresses the phenotype of white petioles caused by an absence or strong reduction of chlorophyll in the petioles.

The invention furthermore relates to hybrid seed and to a method of producing hybrid seed which may comprise crossing a first parent plant with a second parent plant and harvesting the resultant hybrid seed, wherein said first parent plant and/or said second parent plant has the genetic determinant of the invention. The resulting hybrid plant that may comprise the genetic determinant of the invention and shows the trait of the invention is also a plant of the invention.

In one embodiment the plant of the invention which may comprise the genetic determinant either homozygously or heterozygously is a plant of an inbred line, a hybrid, a doubled haploid, or a plant of a segregating population.

In one embodiment, the invention relates to a celery plant that carries the genetic determinant of the invention that leads to the phenotypic trait, and has acquired said determinant by introduction from a suitable source, either by conventional breeding, or genetic modification, in particular by cisgenesis or transgenesis. Cisgenesis is genetic modification of plants with a natural gene, coding for an (agricultural) trait, from the crop plant itself or from a sexually compatible donor plant. Transgenesis is genetic modification of a plant with a gene from a non-crossable species or a synthetic gene.

In one embodiment, the source from which the genetic determinant of the invention is acquired is formed by plants grown from seeds of which a representative sample was deposited under deposit number NCIMB 42428, or from the deposited seeds NCIMB 42428, or from sexual or vegetative descendants thereof, or from another source which may comprise the genetic determinant that leads to the trait of the invention, or from a combination of these sources.

The invention also relates to the germplasm of plants of the invention. The germplasm is constituted by all inherited characteristics of an organism and according to the invention encompasses at least the trait of the invention. The germplasm can be used in a breeding programme for the development of celery plants having an absence or strong reduction of chlorophyll in the petioles. The use of germplasm that may comprise the genetic determinant in breeding is also part of the present invention.

As used herein, a marker is genetically linked to a genetic determinant and can be used for identification of that genetic determinant when the recombination between marker and genetic determinant, i.e. between marker and trait, is less than 5% in a segregating population resulting from a cross between a plant which may comprise the genetic determinant and a plant lacking the genetic determinant.

In one embodiment the invention relates to a marker for identification of the genetic determinant which leads to the absence or strong reduction of chlorophyll in the petioles of a celery plant, which marker is selected from the group of SEQ ID NO. 1, SEQ ID NO. 2, SEQ ID No. 3, and SEQ ID NO. 4. In a preferred embodiment the marker is SEQ ID NO. 1.

In one embodiment the invention relates to the use of a marker for identification of the genetic determinant which leads to the absence or strong reduction of chlorophyll in the petioles of a celery plant, which marker is selected from the group of SEQ ID NO. 1, SEQ ID No. 2, SEQ ID NO. 3, and SEQ ID NO. 4. In a preferred embodiment the marker is SEQ ID NO. 1.

The invention also concerns the use of the genetic determinant leading to the trait of the invention for the development of celery plants that have white petioles, caused by an absence or strong reduction of chlorophyll in the petioles.

The invention also relates to the white celery stalks or petioles that are produced by the plants of the invention. In addition, the invention relates to a food product, which may comprise the white petioles of a celery plant as claimed, or parts thereof, and to the whole marketable celery plant having white petioles without the roots. The invention also relates to a food product in processed form.

In one aspect the invention relates to a method for production of an *Apium graveolens* L. *dulce* plant which may comprise the genetic determinant that leads to an absence or reduction of chlorophyll in the petioles, which may comprise (a) crossing a plant which may comprise the genetic determinant of the invention, representative seed of which plant was deposited as NCIMB 42428, with another plant to obtain an F1 population;
(b) optionally performing one or more rounds of selfing and/or crossing a plant from the F1 to obtain a further generation population;
(c) selecting a plant that may comprise the genetic determinant that results in an absence or reduction of chlorophyll in the petioles in a further generation population, suitably by using a molecular marker linked to the genetic determinant;
(d) optionally performing one or more additional rounds of selfing and/or crossing, and subsequently selecting, for a plant which may comprise the genetic determinant that results in an absence or reduction of chlorophyll in the petioles.

The invention additionally provides a method of introducing another desired trait into a celery plant which may comprise the trait of absent or reduced chlorophyll in the petiole, which may comprise:
(a) crossing a celery plant which may comprise the genetic determinant that leads to absence or reduction of chlorophyll in the petiole, representative seed of which was deposited with the NCIMB under deposit number NCIMB 42428, with a second celery plant that may comprise the other desired trait to produce F1 progeny;
(b) selecting an F1 progeny that may comprise genetic determinants for the absent or reduced chlorophyll in the petiole and for the other desired trait;
(c) crossing the selected F1 progeny with either parent, to produce backcross progeny;
(d) selecting backcross progeny which may comprise genetic determinants for the other desired trait and for the trait of absent or reduced chlorophyll in the petiole; and
(e) optionally repeating steps (c) and (d) one or more times in succession to produce selected third or higher backcross progeny that may comprise the other desired trait and the trait of absent or reduced chlorophyll in the petiole. The invention includes a celery plant produced by this method.

Selecting a plant that may comprise the genetic determinant that results in an absence or reduction of chlorophyll in the petioles in a further generation population can be done phenotypically by observing the color of the petioles or by measuring the chlorophyll content or genetically by determining the presence of the genetic determinant with the use of markers.

Optionally, selfing steps are performed after any of the crossing or backcrossing steps. Selection for a plant which may comprise the genetic determinant of the invention and the desired trait can alternatively be done following any crossing or selfing step of the method.

The invention further provides a method for the production of a celery plant which may comprise the trait of the invention as defined herein by using a doubled haploid generation technique to generate a doubled haploid line that homozygously may comprise the genetic determinant of the invention, which doubled haploid line can be crossed with a line that lacks the said genetic determinant to generate a plant of the invention that may comprise the genetic determinant heterozygously.

The invention also relates to a method for the production of a celery plant which may comprise an absence or strong reduction of chlorophyll in the petioles by using a seed that may comprise the genetic determinant in its genome that leads to the trait of the invention for growing the said celery plant. The seeds are suitably seeds of which a representative sample was deposited with the NCIMB under deposit number NCIMB 42428.

The invention also relates to a method for seed production which may comprise growing celery plants from seeds which may comprise the genetic determinant of the invention, which leads to the phenotypic trait of absence or strong reduction of chlorophyll in the petioles, allowing the plants to produce seeds, and harvesting those seeds. Production of the seeds is suitably done by crossing or selfing. Preferably, the seeds so produced have the capability to grow into plants that have an absence or strong reduction of chlorophyll in the petioles.

In one embodiment, the invention relates to a method for the production of a celery plant which may comprise no or a strongly reduced level of chlorophyll in the petioles by using tissue culture that carries the genetic determinant of the invention in its genome. The invention furthermore relates to a method for the production of a celery plant which may comprise no or a strongly reduced level of chlorophyll in the petioles by using vegetative reproduction of plant material that carries the genetic determinant of the invention in its genome.

In one embodiment, the invention relates to a method for the production of a celery plant which may comprise no or a strongly reduced level of chlorophyll in the petioles by using a method for genetic modification to introduce the genetic determinant of the invention into the celery plant.

The invention provides preferably an *Apium graveolens* L. *dulce* plant which may comprise a dominantly inherited monogenic genetic determinant that leads to white solid petioles due to an absence or strong reduction of chlorophyll, and a growth and/or vigor that is similar to a celery plant having a normal amount of chlorophyll in the petioles. Such a plant is obtainable by any of the methods herein described.

The term 'genetic determinant' as used herein encompasses one or more QTLs, genes or alleles. These terms are used interchangeably.

The 'genetic trait' is the trait or characteristic that is conferred by the genetic determinant. The genetic trait can be identified phenotypically, by observing white petioles, or by measuring the amount of chlorophyll in the petioles. However, also plant stages for which no phenotypic observation can be performed do carry the genetic information that leads to the genetic trait. The genetic trait can also be identified with the use of markers as described herein. 'Trait' or 'phenotypic trait' can be used herein instead of 'genetic trait'.

Equivalence of genetic determinants can be determined by markers as described herein, but can alternatively be determined by an allelism test. To perform an allelism test, material that is homozygous for the known determinant is crossed with material that is also homozygous for its unknown genetic determinant. When no segregation for the trait to be observed is present in the F2 of the cross, the genetic determinants resulting in the phenotypic trait have been proven to be equivalent or the same.

When more than one gene is responsible for a certain trait, and an allelism test is done to determine equivalence, the skilled person doing the test has to ascertain that all relevant genes are present homozygously in order for the test to work properly.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

The invention will be further illustrated in the Examples that follow.

EXAMPLES

Example 1

Creation of Celery Plants of the Invention

In research that led to this invention, a cross was made between 2 fertile plants, one from *Apium graveolens* L. *dulce* (celery) and the other one from *Apium graveolens* var. *secalinum* (smallage). The crosses were made with the use of insects. In the F2 of this specific cross, plants segregated for a large number of characteristics. As expected, the strong points of *dulce*, for which a long period of strict selection focused on the petioles had been performed, where weakened by the genes of *secalinum*, that has been developed in a totally different direction focussed on the leaflets.

*A. graveolens* var. *secalinum* is known for its use of the leaves, and the plants therefore mainly consist of strongly developed leaf blades and thin somewhat brittle petioles. The petioles of this particular material were especially thin, since they were deficient in chlorophyll. In addition, the petioles of this *secalinum* material were hollow. This is totally opposite to *A. graveolens* var. *dulce*, which is specifically grown for the thick, strong, and solid petioles that are used as celery sticks.

Because of the chlorophyll deficiency and therefore the reduction of photosynthesis, it was expected based on common knowledge that plants resulting from this combination that had white petioles would show a reduction in plant vigor and development. Especially when the chlorophyll deficient plant parts would take up a major part of the plants, like the petioles of stalk celery do, the reduction in growth was expected to be critical. However, an attempt was made to continue development, with the aim to introduce white colored, although perhaps weak, petioles and to combine those with the essential petiole characteristics from *dulce*, thereby creating an unexpectedly new type of celery.

Further development was carried out through inbred and half-sib selection. As was observed in earlier programmes, the petiole features of *secalinum*, and especially the hollowness of the petioles, were strongly prevailing and apparently polygenic features that combined dominant with recessive expression. Selection for a plant that would be stable for just having solid petioles proved to be very complicated; the additional features of the petioles being white, as well as other relevant stalk quality aspects, was a complex challenge.

After several cycles however a *dulce* plant was obtained that unexpectedly showed its typical stalk quality and its usual strength and vigor, but had clear white petioles, thereby overcoming the expected growth retardation of the reduced photosynthesis and reduced pigment protection caused by the white colored petioles.

Example 2

Characterisation of Celery Plants of the Invention

Figure 2:
FIG. 2 shows a normal stalk celery plant on the left, and a stalk celery plant of the invention on the right.

Plants of the invention (identified herein as 1002) were compared with common green celery plants of variety Kelvin F1 (1005), Bianco di Sperlonga celery (1004), and a so-called 'Golden' or self-blanching type 'Golden Spartan' (1008), for their chlorophyll content in the petioles. Table 1 shows the results of this comparison. FIG. 2 shows plants of the invention with white petioles on the right, and a normal celery plant on the left.

Celery was sown in week 30, and transplanting was done 8 weeks later in week 38. For the measurement at young plant stage, samples were taken in week 40. For the measurement at mature plant stage, samples were taken in week 52.

To measure the chlorophyll content, the petioles or sticks of 5 celery plants to be measured were cut into pieces of 1-1.5 cm. in length. After this a sample of about 100 g per plant was weighed for use in the measurement. It is possible to freeze the samples at −80° C. until further use.

For the young plants that were measured at 2 weeks after transplanting, the exact weight of the samples was taken and crushed to smaller pieces. Per gram sample 10 ml. of methanol was added, and an Ultra-Turrax was used till the samples were totally crushed.

From the older plants measured at 14 weeks after transplanting first the samples were grinded with liquid nitrogen till they had become powder, and then about 3 g. of the powder was taken. To this, 50 ml. methanol was added.

For both ages the total chlorophyll (chlorophyll a+chlorophyll b) content was measured through determination of the absorption at 653 and 667 nm. These peaks can depend on the solvent that is used in the experiment. Manual correction was performed for fluctuations in baseline. Results and average of five plants are shown in Table 1.

It is clear from the results in Table 1 that the celery plants of the invention are absent or strongly reduced in chlorophyll in the petioles. At mature stage, the chlorophyll content of a plant of the invention is so low that it could not be reliably measured when using this method.

TABLE 1

Chlorophyll content

| | | Chlorophyll content (µg/g) | | | | | |
|---|---|---|---|---|---|---|---|
| | | Plant 1 | Plant 2 | Plant 3 | Plant 4 | Plant 5 | Average |
| 1002 | 2 wks AT | 50 | 28 | 31 | 35 | 20 | 32.9 |
| | 14 wks AT | <4 | <4 | <4 | <4 | <4 | <4 |
| 1005 | 2 wks AT | 258 | 217 | 225 | 192 | 213 | 221.1 |
| | 14 wks AT | 45 | 53 | 60 | 41 | 49 | 49.6 |
| 1004 | 2 wks AT | 141 | 149 | 124 | 140 | 132 | 137.2 |
| | 14 wks AT | 10 | 9 | 4 | 9 | 14 | 9.2 |
| 1008 | 2 wks AT | 121 | 201 | 182 | 183 | 171 | 171.5 |
| | 14 wks AT | 7 | 5 | 6 | 6 | 6 | 5.9 |

Measurement 1 at 2 wks AT is at 2 weeks after transplanting
Measurement 2 at 14 wks AT is at 14 weeks after transplanting

Example 3

Introduction of the New Trait into Other Celery Plants

The plant of the invention as obtained in Example 1 was crossed again with normal celery plants having green petioles. The F2 progeny segregated for plants that showed the same characteristics as the initially developed plant. Further development of this population resulted in segregating populations with the trait of the invention. One (F3) population that proved to be stable for the trait of the invention since the next generation did not segregate anymore was used for the deposit, and a sample of this was deposited as NCIMB 42428. Markers confirmed that these seeds which may comprise the genetic determinant of the invention.

Subsequent crossing of plants that resulted from the same genotype as the deposited seeds were crossed again with a celery plant that had green petioles, and therefore did not have the genetic determinant of the invention. As expected, all the plants of the F1 resulting from this cross were strongly reduced in chlorophyll, and therefore showed white petioles. The F1 plants were crossed with each other to generate an F2 population, which segregated for plants having green and plants having white petioles. The markers that are mentioned in this application distinguish in the white F2 plants between plants having the genetic determinant homozygously, and plants having the genetic determinant heterozygously.

The invention is further described by the following numbered paragraphs:

1. Celery plant (*Apium graveolens* L. *dulce*) carrying a genetic determinant that leads to an absence or strong reduction of chlorophyll in the petioles, which genetic determinant is as comprised in an *Apium graveolens* L. *dulce* plant, representative seed of which was deposited with the NCIMB under deposit number NCIMB 42428.

2. A celery plant of paragraph 1, wherein the genetic determinant can be identified by any of the markers having SEQ ID NO. 1, SEQ ID NO. 2, SEQ ID NO. 3, and/or SEQ ID NO. 4, preferably by SEQ ID NO. 1.

3. A celery plant of paragraph 1 or 2, wherein the genetic determinant is introgressed from a plant comprising said genetic determinant, representative seed of which was deposited with the NCIMB under deposit number NCIMB 42428.

4. A celery plant of any of the paragraphs 1-3, which has a similar growth and/or vigor as compared to a celery plant that has no reduction of chlorophyll in the petioles.

5. A celery plant of any of the paragraphs 1-4, obtainable by crossing a first celery plant with a second celery plant, wherein at least one of the said plants is grown from seed that carries the genetic determinant, representative seed of which was deposited with the NCIMB under deposit number NCIMB 42428, or a progeny plant thereof, optionally crossing the resulting F1, and selecting for plants that have an absence or strong reduction of chlorophyll in the petioles, optionally followed by one or more additional rounds of crossing and/or selection.

6. Celery plant of any one of the paragraphs 1-5, wherein the average total chlorophyll content in the petioles of a plant at 2 weeks after transplanting in order of increased preference is lower than 100 µg/g, 80 µg/g, 60 µg/g, 40 µg/g.

7. Celery plant of any of the paragraphs 1-6, wherein the average total chlorophyll content in the petioles of a plant at 14 weeks after transplanting is <4 µg/g.

8. *Apium graveolens* L. *dulce* seed, wherein the plant that can be grown from the seed comprises the genetic determinant that leads to an absence or strong reduction of chlorophyll in the petioles.

9. Progeny of an *Apium graveolens* L. *dulce* plant of any one of the paragraphs 1-6, or of seed of paragraph 7, comprising the genetic determinant that leads to an absence or strong reduction of chlorophyll in the petioles as comprised in an *Apium graveolens* L. *dulce* plant, representative seed of which was deposited with the NCIMB under deposit number NCIMB 42428.

10. Propagation material suitable for producing a plant of any one of the paragraphs 1-6 and 8, wherein the propagation material is suitable for sexual reproduction, and is in particular selected from microspores, pollen, ovaries, ovules, embryo sacs and egg cells, or is suitable for vegetative reproduction, and is in particular selected from cuttings, roots, stems, cells, protoplasts, or is suitable for tissue cultures of regenerable cells, and is in particular selected from leaves, pollen, embryos, cotyledon, hypocotyls, meristematic cells, roots, root tips, anthers, flowers, seeds and stems, wherein the plant produced from the propagation material comprises the genetic determinant that leads to an absence or strong reduction of chlorophyll in the petioles as comprised in an *Apium graveolens* L. *dulce* plant, representative seed of which was deposited with the NCIMB under deposit number NCIMB 42428.

11. Food product, comprising the white petioles of a celery plant of any of the paragraphs 1-6 and 8-9, or parts thereof, or the whole marketable celery plant having white petioles without the roots, optionally in processed form.

12. Marker for identification of the genetic determinant that leads to an absence or strong reduction of chlorophyll in the petioles of an *Apium graveolens* L. *dulce* plant, which marker is selected from the group consisting of SEQ ID NO. 1, SEQ ID NO. 2, SEQ ID NO. 3, and SEQ ID NO. 4.

13. Use of a marker for identification of the genetic determinant that leads to an absence or strong reduction of chlorophyll in the petioles of an *Apium graveolens* L. *dulce* plant, which marker is selected from the group of SEQ ID NO. 1, SEQ ID NO. 2, SEQ ID NO. 3, and SEQ ID NO. 4.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A celery plant (*Apium graveolens* L. *dulce*) carrying a genetic determinant that leads to an absence or strong reduction of chlorophyll in the petioles, which genetic determinant is as comprised in an *Apium graveolens* L. *dulce* plant, representative seed of which was deposited with the NCIMB under deposit number NCIMB 42428, wherein the genetic determinant can be identified by a marker having SEQ ID NO: 1 and wherein the average total chlorophyll content in the petioles of a plant at 14 weeks after transplanting is <4 μg/g.

2. The celery plant as claimed in claim 1, wherein the genetic determinant is introgressed from a plant comprising said genetic determinant, representative seed of which was deposited with the NCIMB under deposit number NCIMB 42428.

3. The celery plant as claimed in claim 1, which has a similar growth and/or vigor as compared to a celery plant that has no reduction of chlorophyll in the petioles.

4. The celery plant as claimed in claim 1, obtainable by crossing a first celery plant with a second celery plant, wherein at least one of the said plants is grown from seed that carries the genetic determinant, representative seed of which was deposited with the NCIMB under deposit number NCIMB 42428, or a progeny plant thereof, optionally crossing the resulting F1, and selecting for plants that have an absence or strong reduction of chlorophyll in the petioles, optionally followed by one or more additional rounds of crossing and/or selection.

5. The celery plant as claimed in claim 1, wherein the average total chlorophyll content in the petioles of a plant at 2 weeks after transplanting is lower than 40 μg/g.

6. An *Apium graveolens* L. *dulce* seed, representative seed of which was deposited with the NCIMB under deposit number NCIMB 42428 wherein a plant that can be grown from the seed comprises a genetic determinant that leads to an absence or strong reduction of chlorophyll in the petioles, wherein the genetic determinant can be identified by a marker having SEQ ID NO: 1 and wherein the average total chlorophyll content in the petioles of a plant at 14 weeks after transplanting is <4 μg/g.

7. A progeny of an *Apium graveolens* L. *dulce* plant as claimed in claim 1, or of a plant grown from the seed as claimed in claim 6, comprising the genetic determinant that leads to an absence or strong reduction of chlorophyll in the petioles as comprised in an *Apium graveolens* L. *dulce* plant, representative seed of which was deposited with the NCIMB under deposit number NCIMB 42428.

8. A propagation material suitable for producing the plant as claimed in claim 1 or a plant grown from the seed as claimed in claim 6, wherein the propagation material is suitable for sexual reproduction or is suitable for vegetative reproduction, or is suitable for tissue cultures of regenerable cells, wherein the plant produced from the propagation material comprises the genetic determinant that leads to an absence or strong reduction of chlorophyll in the petioles as comprised in an *Apium graveolens* L. *dulce* plant, representative seed of which was deposited with the NCIMB under deposit number NCIMB 42428.

9. The propagation material as claimed in claim 8, wherein the propagation material suitable for sexual reproduction is selected from microspores, pollen, ovaries, ovules, embryo sacs and egg cells.

10. The propagation material as claimed in claim 8, wherein the propagation material suitable for vegetative reproduction is selected from cuttings, roots, stems, cells, protoplasts.

11. The propagation material as claimed in claim 8, wherein the propagation material suitable for tissue cultures of regenerable cells is selected from leaves, pollen, embryos, cotyledon, hypocotyls, meristematic cells, roots, root tips, anthers, flowers, seeds and stems.

12. The celery plant as claimed in claim 1, wherein the average total chlorophyll content in the petioles of a plant at 2 weeks after transplanting is lower than 60 µg/g.

13. The celery plant as claimed in claim 1, wherein the average total chlorophyll content in the petioles of a plant at 2 weeks after transplanting is lower than 80 µg/g.

14. The celery plant as claimed in claim 1, wherein the average total chlorophyll content in the petioles of a plant at 2 weeks after transplanting is lower than 100 µg/g.

* * * * *

SEQUENCE LISTING

```
<160> NUMBER OF SEQ ID NOS: 4

<210> SEQ ID NO 1
<211> LENGTH: 290
<212> TYPE: DNA
<213> ORGANISM: Apium graveolens
<220> FEATURE:
<221> NAME/KEY: source
<222> LOCATION: 1..290
<223> OTHER INFORMATION: /organism="Apium graveolens"
      /mol_type="unassigned DNA"
```

```
<220> FEATURE:
<221> NAME/KEY: misc_feature
<222> LOCATION: 3
<223> OTHER INFORMATION: /note="w = a or t"
<220> FEATURE:
<221> NAME/KEY: misc_feature
<222> LOCATION: 5
<223> OTHER INFORMATION: /note="r = g or a"

<400> SEQUENCE: 1
ttwargcagt gtggatacct cagattgaat agccacactt ttgctcacaa ggtcagtggt    60
ggttattgca acagctgccg aatctgccct attgaaaaca agatctacg tttcagatag    120 gatatgaaga ataataaaat gatcatgcta tctacatctg taattagaaa aacatagaga    180
gcaaaaatga ctgccaaaaa atttcaacgg aaaacagatc caacatatat agtaagtgct    240
ctgtaaatca gttttccgca tgatatcagg tgaaaaagtg taccctgcag                290

<210> SEQ ID NO 2
<211> LENGTH: 469
<212> TYPE: DNA
<213> ORGANISM: Apium graveolens
<220> FEATURE:
<221> NAME/KEY: source
<222> LOCATION: 1..469
<223> OTHER INFORMATION: /organism="Apium graveolens"
      /mol_type="unassigned DNA"
<220> FEATURE:
<221> NAME/KEY: misc_feature
<222> LOCATION: 55
<223> OTHER INFORMATION: /note="r = g or a"
<220> FEATURE:
<221> NAME/KEY: misc_feature
<222> LOCATION: 170
<223> OTHER INFORMATION: /note="k = g or t"
<220> FEATURE:
<221> NAME/KEY: misc_feature
<222> LOCATION: 201
<223> OTHER INFORMATION: /note="k = g or t"
<220> FEATURE:
<221> NAME/KEY: misc_feature
<222> LOCATION: 385
<223> OTHER INFORMATION: /note="y = t or c"

<400> SEQUENCE: 2
ttaaccatca ttgattatga tcttgtttta tcgaattata ttgtttatca tattraactg    60
ctttaggatt ggatagtttt tatatatgtg gaccagattc gtggtcagac cataccaatg   120
gtcaagttag gccaatgtgt gccttggatc cagtaattag agcagtgttk tgtgcttgct   180
cggggttagt gcgtgactga kcagcagcct aaccttggtt tttaaaactt aaatatgctg   240
tgaaagaata agatccacac tcctattact ataatttctt tgaagattgt caaataactc   300
attctttgaa gcatgtgcag aaattttagt ctgacaaaat acagaaggga attggaaaat   360
tggtttagtg taactagact agtcytgata atgcatcgaa gttcagtgat agaatgcaaa   420
gaaccatata tccaaaaatt ctatatcaaa gctagatcag tacctgcag              469

<210> SEQ ID NO 3
<211> LENGTH: 261
<212> TYPE: DNA
<213> ORGANISM: Apium graveolens
<220> FEATURE:
<221> NAME/KEY: source
<222> LOCATION: 1..261
<223> OTHER INFORMATION: /organism="Apium graveolens"
      /mol_type="unassigned DNA"
<220> FEATURE:
<221> NAME/KEY: misc_feature
<222> LOCATION: 27
```

```
<223> OTHER INFORMATION: /note="r = g or a"
<220> FEATURE:
<221> NAME/KEY: misc_feature
<222> LOCATION: 28
<223> OTHER INFORMATION: /note="k = g or t"
<220> FEATURE:
<221> NAME/KEY: misc_feature
<222> LOCATION: 36
<223> OTHER INFORMATION: /note="k = g or t"
<220> FEATURE:
<221> NAME/KEY: misc_feature
<222> LOCATION: 37
<223> OTHER INFORMATION: /note="k = g or t"

<400> SEQUENCE: 3
ttaaaataat tgtggaggta aactgarktt tttttkkcta agtaaactca cacacacaca     60
ggggttgaac ccttgacctc ctccagagga ggcaagagct caagcactgc accaaccctt    120
tgttggcaag gtaagcagag ttattcacaa acaaatgtct acttttttct gatcgagcag    180
aagttagctc atttgcagat gaatgtgtga gaatgtccaa taatttaggc acctttgaag    240
aaatcaccta tttccctgca g                                              261

<210> SEQ ID NO 4
<211> LENGTH: 253
<212> TYPE: DNA
<213> ORGANISM: Apium graveolens
<220> FEATURE:
<221> NAME/KEY: source
<222> LOCATION: 1..253
<223> OTHER INFORMATION: /organism="Apium graveolens"
      /mol_type="unassigned DNA"

<400> SEQUENCE: 4
ctgcaggtac tacaattaga atctaaattg ctcaggtaca gaaaaggttt agtgaacgat     60
ttctaaaacc aggatggtga aattggacca caagattttg tatcatctct ggtttcatac    120
taaaagtaga tttatactaa cacttatttg gcccatttaa taatcataaa catgagaaaa    180
aagataaacc ataataattt acttgtatag aattagaaga aaccagaaca tgataggata    240
taataagtca gtg                                                       253
```